United States Patent
Haven et al.

[11] Patent Number: 5,827,418
[45] Date of Patent: Oct. 27, 1998

[54] ELECTROPHORESIS CASSETTE

[75] Inventors: Kenneth R. Haven, Fremont, Calif.; Sören Eriksson, Uppsala, Sweden

[73] Assignee: Hoefer Pharmacia Biotech, Inc., San Francisco, Calif.

[21] Appl. No.: 745,654

[22] Filed: Nov. 8, 1996

Related U.S. Application Data

[60] Provisional application No. 60/028,314 Oct. 11, 1996.
[51] Int. Cl.⁶ .......................... G01N 27/26; G01N 27/447
[52] U.S. Cl. .......................... 204/618; 204/466; 204/467; 204/616
[58] Field of Search .................................. 204/618, 616, 204/467, 466

[56] References Cited

U.S. PATENT DOCUMENTS

| | | | |
|---|---|---|---|
| 4,954,236 | 9/1990 | Kushner et al. | 204/466 |
| 5,288,465 | 2/1994 | Margolis | 422/102 X |
| 5,407,552 | 4/1995 | Lebacq | 204/619 |
| 5,411,657 | 5/1995 | Leka | 204/618 |
| 5,543,023 | 8/1996 | Lugojan | 204/618 |

*Primary Examiner*—Robert J. Warden
*Assistant Examiner*—John S. Starsiak, Jr.
*Attorney, Agent, or Firm*—Limbach & Limbach L.L.P.

[57] ABSTRACT

An electrophoresis gel cassette that includes a bottom plate with an attached base portion, a cover plate, and a gel chamber formed between the two plates. There is at least one opening, which is in communication with the gel chamber, encompassed in the base portion, thereby making the opening seamless or free of parting lines. Upon assembling the cassette, a contact face of the base portion of the bottom plate and a contact face of the cover plate can be sealed by sonic welding or adhesives to produce a water-tight seal and to facilitate casting.

5 Claims, 5 Drawing Sheets

ELECTROPHORESIS CASSETTE

This application claims the benefit of U.S. Provisional application No. 60/028,314 filed Oct. 11, 1996 by Express Mail No. EM345443143US, which is incorporated herein by reference. The title of the prior provisional application is "Electrophoresis Cassette" the inventors are Kenneth R. Haven and Sören Eriksson and the Attorney Docket No. is HOE-5000.

BACKGROUND

The invention relates to a gel electrophoresis cassette. More specifically, the invention relates to a gel electrophoresis cassette that provides maximal gel length while being simple to manufacture, reliable to seal for casting, and easy to use.

Casting polyacrylamide gels for vertical electrophoresis is commonly done by creating a mold formed of two glass plates separated by thin plastic spacers at the edges. The bottom of the mold may be sealed with tape, another spacer, or by compression against a gasket. Once sealed on the edges and bottom, a solution of acrylamide, polymerization catalysts and buffers are introduced into the mold and allowed to polymerize. After the gel has formed, the seal on the bottom is removed to provide an electrical contact for electrophoresis. Automating this casting procedure is a means of reducing cost, user labor, and improving reproducibility.

Molded plastic cassettes have been described by a number of inventors including Leka, U.S. Pat. No. 5,411,657 (Jule, snap-off bottom); Lebaq, U.S. Pat. No. 5,407,522 (Bioprobe, one piece); Margolis, U.S. Pat. No. 5,288,465 (Gradipore); Kushner, et al., U.S. Pat. No. 4,954,236 (Bio-Rad, hybrid); or have been introduced commercially (Novex).

The sealing of the mold on three edges is conveniently done in one step by ultrasonic welding, such as exemplified by Leka. However, to open the bottom, Leka provides a weakened line along which the bottom seal can be broken away. Breaking off the bottom seal requires substantial force and, in the hands of inexperienced user, often damages the gel in the upper part of the cassette or leaves irregular edges.

Novex also seals the three edges by ultrasonic welding, but leaves an opening along the bottom edge of one face of the mold. During casting, the opening is sealed with a piece of tape. The tape is convenient to remove for running the gel, but the resultant gel is L-shaped, with a "foot" protruding from one surface of the gel. This is inconvenient for drying or blotting the gel after samples have been electrophoresed. Another drawback to the Novex design is that the seal area below the foot reduces the separation length possible compared to a conventional cassette of the same dimensions.

Kushner, et al, describe a two-plate system in which a flat plate is sealed to a molded, cavity-forming plate by use of a waterproof tape. Removing the area of tape between the bottom edge of the flat plate and the lower sealing rib of the molded plate exposes the lower edge of the gel. The resultant gel has the same protruding "foot" as seen in the Novex gels.

Margolis describes a two-piece un-welded design which has no L-shaped foot and is readily opened, but the bottom edge is difficult to seal with a simple application of tape because of the presence of seams where the two halves meet. The product as sold seems to be designed not to be sealed at the bottom. Gels can be cast through the open bottom, but it requires an additional casting tank.

Lebaq describes a one-piece cassette, in which the top is sealed by inserting a comb, thus allowing the gel to be cast upside down. Using a comb as a sealing piece often makes the comb difficult to extract. More objectionable for most users is that the cassette is not readily opened for subsequent treatment of the gel, such as staining or blotting.

Thus, there is a need for a gel electrophoresis cassette that does not require a break off bottom seal; does not require an L-shaped, shortened separation length gel; does not have a bottom seam that makes tape sealing difficult; and does not need to be cast upside down with combs and that can be easily opened for subsequent gel treatment. In addition to these requirements, there is a need for a gel electrophoresis cassette that is easy to use, reliable, provides the maximum gel length and is simple to manufacture.

SUMMARY

The present invention addresses the above needs by supplying an electrophoresis gel cassette that includes a bottom plate and a cover plate which define a gel chamber therebetween. The gel chamber defines a gel chamber plane. The cassette further includes a bottom plate base portion which is connected to the bottom plate. The base portion includes an opening therethrough, and the opening defines an opening plane that is generally parallel to the gel chamber plane. In a preferred embodiment the bottom plate has an outer face and the bottom plate base portion has an outer face which meets the bottom plate outer face at an included angle of greater that ninety degrees. In another embodiment the bottom plate base portion may include a bottom wall connected to the bottom plate, a top wall, and first and second side walls connecting the top and bottom walls. In this embodiment the top, bottom and side walls define the opening through the bottom plate base portion. In another embodiment the cover plate and bottom plate base portion may include contact faces that contact each other at a seal plane. These contact faces may be sealed, e.g. by sonic welding or adhesives to produce a water-tight seal and to facilitate casting. The seal plane may be spaced apart from the bottom plate base portion opening.

The electrophoresis gel cassette may be fabricated from a cover plate and a bottom plate having an attached bottom plate base portion. The cover plate and bottom plate include contact faces and may be as describe above. The fabrication process further includes positioning the contact faces proximal to each other and positioning the bottom plate spaced apart from the cover plate, defining a gel chamber therebetween. The gel chamber defines a plane that is generally parallel to the bottom plate base portion opening plane. The process also includes sealing the contact faces, e.g. by sonically welding or the application of adhesive to the contact faces to produce a water-tight seal.

BRIEF DESCRIPTION OF THE FIGURES

In these Figures, like numbers designate the same or similar elements.

DETAILED DESCRIPTION

Figure 1:
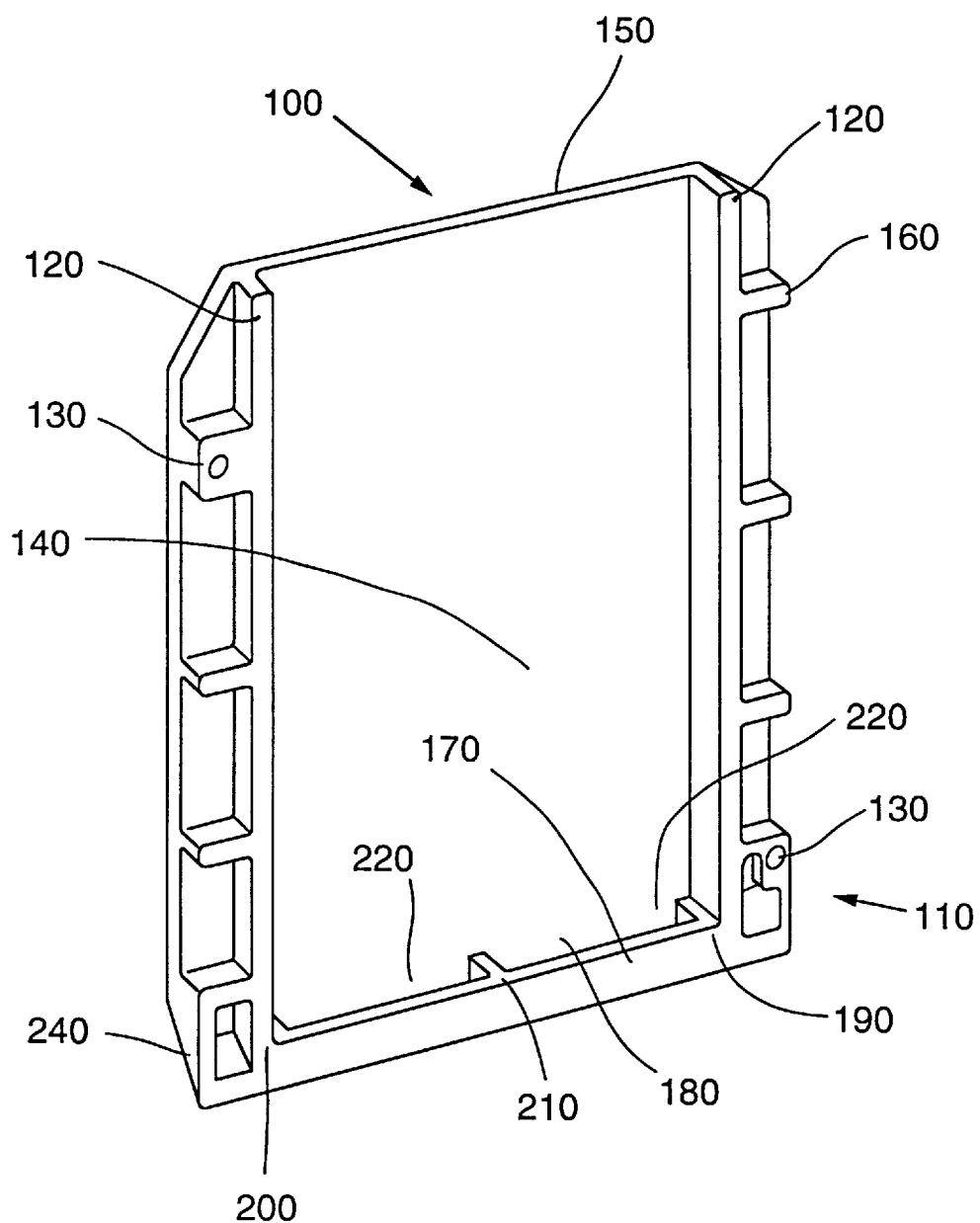
FIG. 1 shows a perspective view of one embodiment of a bottom plate for a gel cassette according to the present invention.
Figure 2:
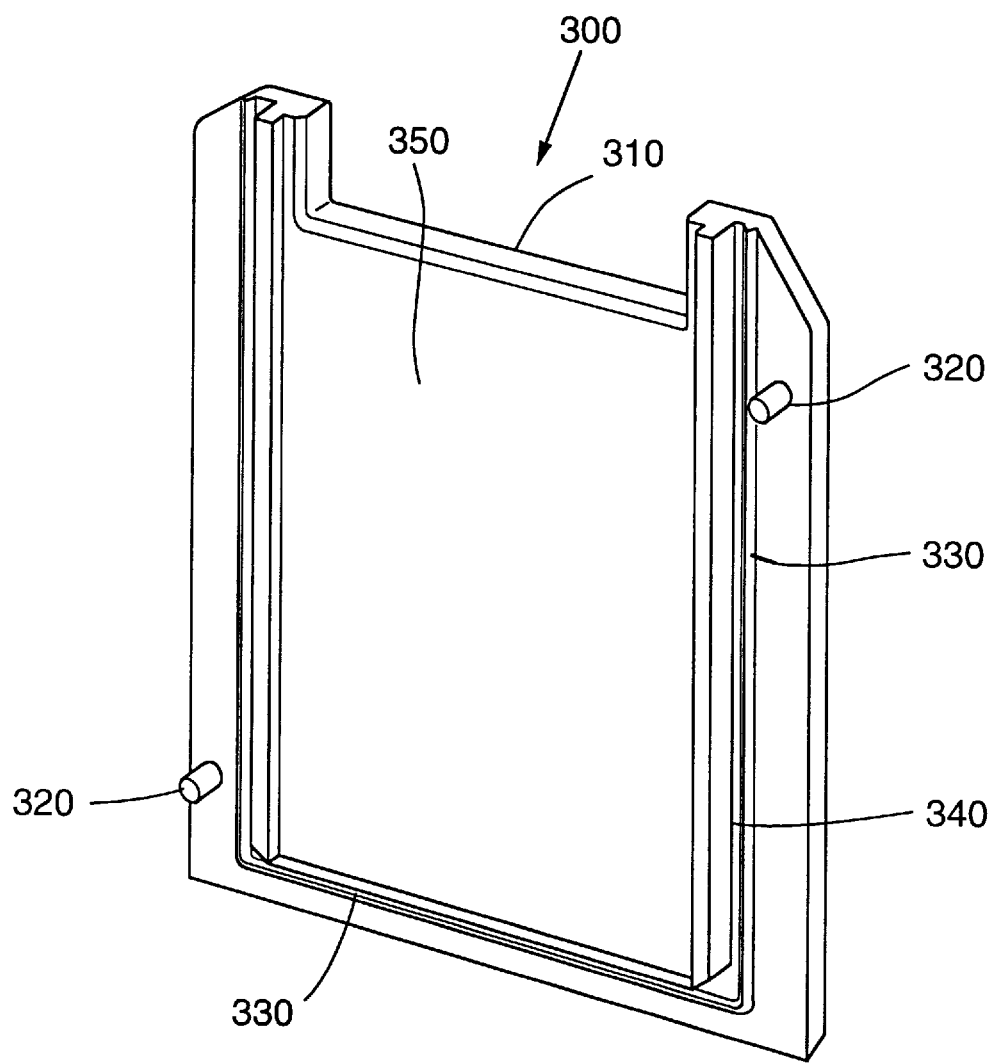
FIG. 2 shows a perspective view of one embodiment of a cover plate for a gel cassette according to the present invention.
Figure 3:
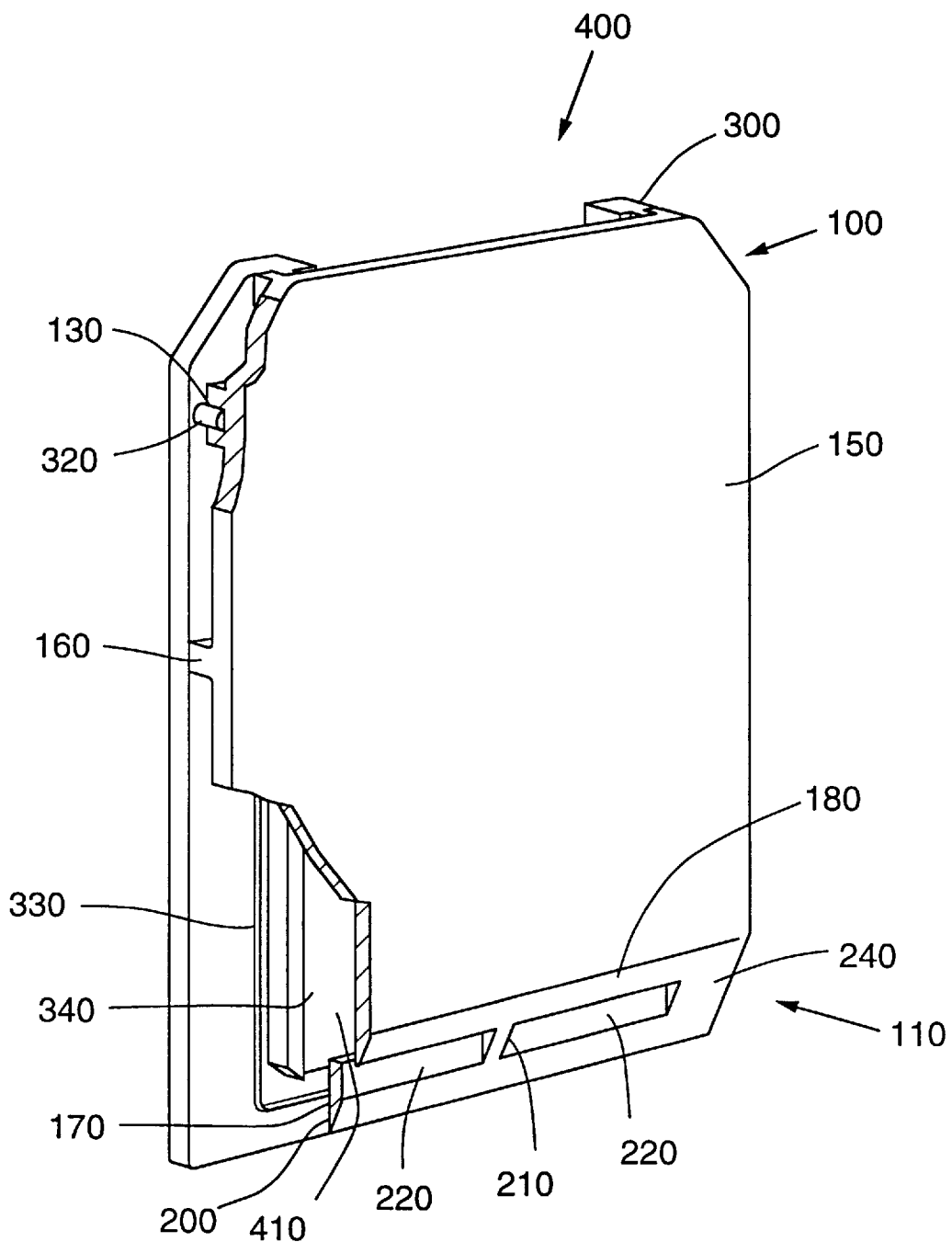
FIG. 3 shows a partially cut away perspective view of one embodiment of an assembled gel cassette according to the present invention.

The present invention provides an electrophoresis gel cassette one embodiment of which includes a bottom plate and a cover plate. FIGS. 1, 2, and 3 show one such embodiment: FIG. 1 shows a perspective view of one example of a bottom plate; FIG. 2 shows a perspective view of one example of a cover plate; and FIG. 3 shows a perspective, partially cut-away view of an assembled gel cassette including the bottom and cover plates of FIGS. 1 and 2 respectively.

FIG. 1 shows a bottom plate 100 according to the present invention that includes a bottom plate base portion 110. The bottom plate includes side welding surfaces 120, alignment sockets 130, inner face 140, outer face 150, and edge stiffeners 160. The base portion 110 includes a top wall 170, a bottom wall 180, and side walls 190 and 200. The bottom plate base portion may also include an optional support wall 210. The bottom plate base portion 110 also includes opening or openings 220 therethrough and an outer face 240. The openings define an opening plane which is shown more clearly in FIGS. 4 and 5 below. The support wall 210 may prevent bowing of the top wall during assembly of the cassette or during electrophoresis.

FIG. 2 shows a cover plate 300 according to the present invention that includes an upper buffer contact notch 310, alignment pins 320, weld director 330, spacer 340, and inner face 350. The upper buffer contact notch 310 provides the point of contact between an upper electrophoresis buffer and gel cast in the cassette. The upper buffer contact notch 310 is also the point of insertion of combs to form sample wells during casting and polymerization of a gel in the cassette. The alignment pins 320 insert into the alignment sockets 130 of the bottom plate when the cassette is assembled. The weld director 330 is essentially a thin rib of material extending along the sides and bottom portion of the cover plate 300 which contacts the side welding surfaces 120 and top wall 170 when the cassette is assembled. The spacer 340 determines the thickness of the gel by establishing the distance between the inner face of the bottom plate 140 and the inner face of the cover plate 350 when the cassette is assembled. The edge stiffener 160 is included on the sides of the bottom plate 100 to prevent bowing of the plates 100 and 300 due to pivoting across the weld when the cassette is clamped by its edges into an electrophoresis unit.

FIG. 3 shows an assembled electrophoresis gel cassette 400 according to the present invention that includes bottom plate 100 and cover plate 300 which define a gel chamber 410 therebetween. The gel chamber 410 defines a gel chamber plane which is shown more clearly in FIG. 5 below.

Figure 4:
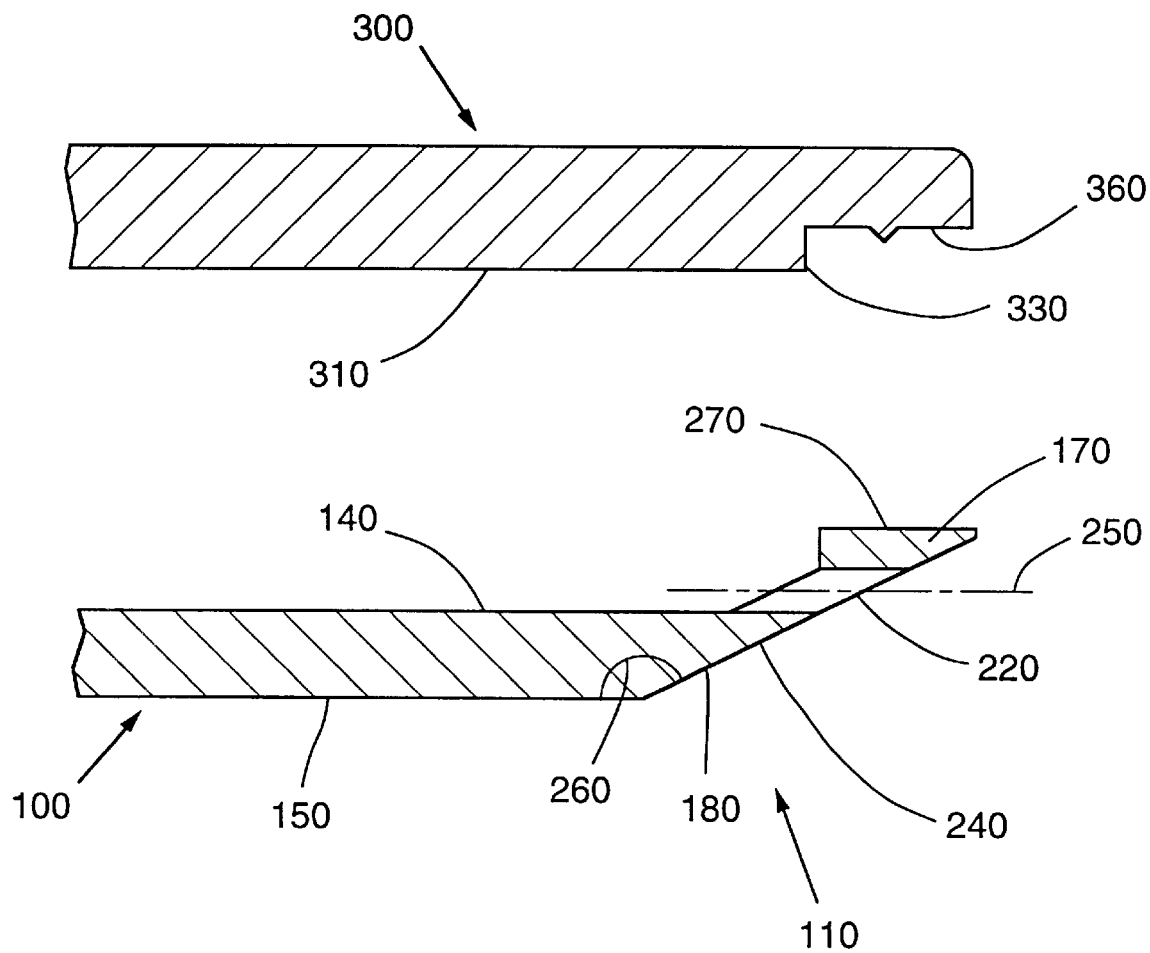
FIG. 4 shows a cross-sectional view of one embodiment of unassembled bottom and cover plates according to the present invention.
Figure 5:
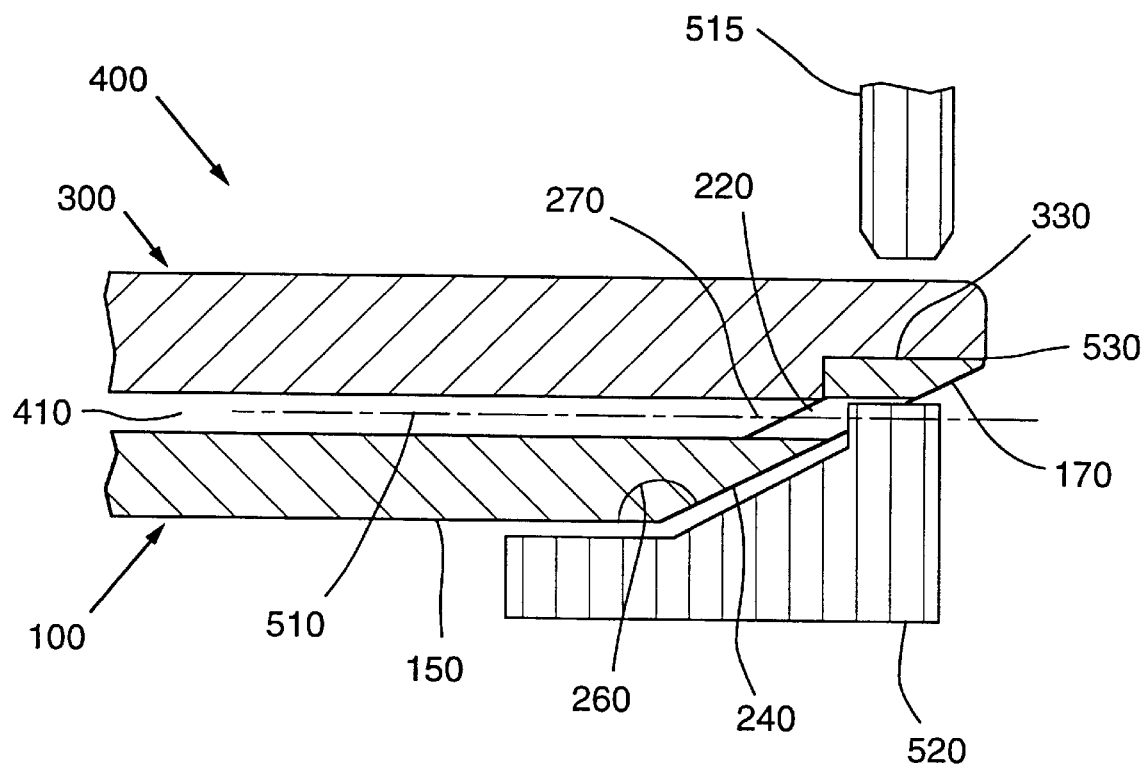
FIG. 5 shows a cross-sectional view of one embodiment of an assembled gel cassette according to the present invention.

FIGS. 4 and 5 show cross-sectional views of a portion of the bottom and cover plates shown in FIGS. 1 and 2 respectively. FIG. 4 shows the plates prior to assembly and FIG. 5 shows the assembled gel cassette.

FIG. 4 shows the bottom plate 100 attached to the bottom plate base portion 110 which includes top wall 170, bottom wall 180 and opening 220 through the bottom plate base portion. The opening 220 defines an opening plane 250. The bottom plate base portion 110 also includes an outer face 240 that meets the bottom plate outer face 150 at an included angle 260. FIG. 4 shows a preferred embodiment in which the included angle 260 is greater than 90 degrees; however, the invention also includes embodiments in which the included angle 260 may be 90 degrees or less. The bottom plate base portion 110 also includes a contact surface 270 which contacts cover plate contact surface 360 when the cassette is assembled. FIG. 4 shows an embodiment in which the cover plate contact surface 360 includes the weld director 330 thereon and the bottom plate base portion top wall 170 includes the bottom plate contact surface 270.

FIG. 5 shows bottom plate 100 and cover plate 300 assembled to give the gel cassette 400. When assembled bottom plate 100 and cover plate 300 define a gel chamber 410 that defines a gel chamber plane 510. According to the present invention the gel chamber plane 510 is generally parallel to the opening plane 330 defined by the bottom plate base portion opening 220. FIG. 5 shows a preferred embodiment in which the planes are parallel which allows for maximum gel length; however, embodiments in which the planes are not exactly parallel are also understood to be within the scope of the invention. Deviations from the planes being substantially parallel will decrease the gel length but so long as the planes are not at 90 degrees the gel length of the invention is longer and therefore superior to the conventional L-shaped gel cassettes.

FIG. 5 also shows one example of a process for assembling the gel cassette 400. In this embodiment, the process uses a sonic welding to seal the plates 100 and 300. The plates 100 and 300 are sonically welded conventionally along the two sides of the plates, i.e. along side welding surfaces 120. As is conventional, the weld director is liquefied by heat from the applied sonic energy and forms a water-tight seal between the plates. Regarding sealing the bottom plate base portion to the cover plate, FIG. 5 shows a preferred embodiment that includes a sonic welder horn 515 and sonic welder nest 520. During assembly, the weld director 330 is liquefied by heat from sonic energy applied through the sonic welder horn 515 to form a water-tight seal 530 between the bottom plate base portion and cover plate contact surfaces, 270 and 360 respectively. FIG. 5 shows an embodiment of the invention in which the bottom plate base portion outer face 240 makes an obtuse included angle 260 with the bottom plate outer face 150. Such an embodiment simplifies the welding step. The angled face 240 allows the bottom plate base portion 110 to be placed on a sonic welder nest 520 which supports the top wall 170 during the welding process. Because of the angled face 240, no moving nest support arm or sliding of the cassette parts is required to provide a secure support for the top wall 170.

FIG. 5 shows that in the assembled cassette, opening 220 through the base portion 110 allows gel and electric current to flow in a plane 270 generally the same as the plane of the gel chamber 510. The opening 220 can be covered with tape during casting, then exposed by removing the tape when the gel is to be used. FIG. 5 shows an embodiment of the gel cassette in which the outer face 240 of the base portion of the bottom plate has no part lines or seams to interfere with tape sealing, as can also be seen in FIG. 3.

FIGS. 1, 2 and 3 show an embodiment of the invention in which the cover plate 300 includes alignment pin 320 which corresponds to alignment sockets 130 located on the bottom plate 100. When seated in the alignment sockets 130, the pins 320 prevent the cover plate 300 from sliding sideways relative to the bottom plate 100 when pressure is applied to compress the weld director 330 as it is melted by the application of sonic energy through the sonic welder horn 515. The pins 320 and sockets 130 combination thus increases the precision of welding, resulting in more reproducible sealing of the cassette and more reproducible uniform gel thickness when casting the gel.

We claim:

1. An electrophoresis gel cassette, comprising:

a bottom piece;

an elongated hexahedron base having a tetragonel cross section, the base having a lower face, an inner face parallel to an outer face, and an upper face perpendicular to the inner and outer faces, the base being integrally connected at it ends to an end of the bottom piece so that, wherein the inner face of the base opposes and is spaced apart from an inner face of the bottom piece to define at least one opening therebetween, the opening having an axis that defines an opening plane which is substantially parallel to the plane of the bottom piece and extending to full length of the inner face of the bottom piece where the lower face of the base and a lower face of the bottom piece meet; and a cover piece having an inner face that is spaced apart from the inner face of the bottom piece and the outer face of the base in an overlying relationship to define a gel chamber therebetween, wherein the gel chamber defines a plane aligned with the opening plane, has a useable length determined by the full length of the inner face of the bottom piece and communicates with the at least one opening in substantially the same plane.

2. An electrophoresis gel cassette according to claim 1, wherein the intersection of a plane defined by an outer face of the bottom piece and a plane defined by the lower face of the base forms an included angle of greater than ninety degrees.

3. An electrophoresis gel cassette according to claim 1, wherein the cover piece has a contact face that opposes the outer face of the base and the contact face and the outer face of the base are sonically welded to each other to produce a water-tight seal.

4. A process for making an electrophoresis gel cassette, the process comprising the steps of:

(a) providing a bottom piece integrally attached to an elongated hexahedron of tetragonal cross section base, the base including a lower face, an inner face parallel to an outer face, and an upper face perpendicular to the inner face and the outer face, wherein the inner face of the base opposes and is spaced apart from an inner face of the bottom piece to form at least one opening therebetween, the opening having an axis that defines an opening plane that is substantially parallel to the plane of the bottom piece and extending to an intersection of the lower face of the base and a lower face of the bottom piece;

(b) contacting the outer face of the base with an opposing contact face on the cover piece so that an inner face of the bottom piece and an inner face of the cover piece are spaced apart in an overlying relationship and define a gel chamber therebetween, the gel chamber defining a plane that is aligned with the opening plane, having a useable length determined by the full length of the inner face of the bottom niece and communicating with the at least one opening in substantially the same name; and (c) sealing the contact face of the cover plate and the inner face of the base to produce a water-tight seal.

5. A process for making an electrophoresis gel cassette according to claim 4, wherein the sealing step comprises sonic welding.

* * * * *